(12) United States Patent
Farrell et al.

(10) Patent No.: US 12,420,056 B2
(45) Date of Patent: Sep. 23, 2025

(54) SLEEVED HYDROPHILIC MEDICAL PRODUCTS

(71) Applicant: Hollister Incorporated, Libertyville, IL (US)

(72) Inventors: David J Farrell, Ballina (IE); Satwinder S. Panesar, Foxford (IE); Carlos Horkan, Westport (IE); Michael G. Murray, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 884 days.

(21) Appl. No.: 17/637,957

(22) PCT Filed: Aug. 27, 2020

(86) PCT No.: PCT/US2020/048234
§ 371 (c)(1),
(2) Date: Feb. 24, 2022

(87) PCT Pub. No.: WO2021/041703
PCT Pub. Date: Mar. 4, 2021

(65) Prior Publication Data
US 2022/0280751 A1    Sep. 8, 2022

Related U.S. Application Data

(60) Provisional application No. 62/912,229, filed on Oct. 8, 2019, provisional application No. 62/892,301, filed on Aug. 27, 2019.

(51) Int. Cl.
*A61M 25/00*    (2006.01)
*A61M 25/01*    (2006.01)

(52) U.S. Cl.
CPC ...... *A61M 25/002* (2013.01); *A61M 25/0017* (2013.01); *A61M 25/007* (2013.01); *A61M 25/0097* (2013.01); *A61M 25/01* (2013.01)

(58) Field of Classification Search
CPC ............ A61M 25/002; A61M 25/0017; A61M 25/007; A61M 25/0097; A61M 25/01;
(Continued)

(56) References Cited

U.S. PATENT DOCUMENTS 4,170,996 A    10/1979  Wu
4,863,441 A *   9/1989  Lindsay ............ A61M 25/0054
                                                      604/523

(Continued)

FOREIGN PATENT DOCUMENTS

CN    218685683 U    3/2023
WO    2016182695 A1  11/2016
WO    2023180702 A1   9/2023

OTHER PUBLICATIONS

International Search Report and Written Opinion for International Application No. PCT/US2020/048234 Dated Dec. 8, 2020.

*Primary Examiner* — Adam Marcetich
(74) *Attorney, Agent, or Firm* — Cook Alex Ltd.

(57) ABSTRACT

A sleeved hydrophilic catheter (10) with a sleeve (22) containing a hydration liquid. It comprises a catheter tube having a proximal end portion (14) and a distal end portion (16), the catheter tube having a side wall (19) defining a lumen. A drainage opening (17) is located in the distal end portion (16) of the catheter tube and through the side wall (19) of the catheter tube, the drainage opening (17) being in communication with a cavity of the sleeve (22) and the lumen of the catheter tube. A deflection member is associated with the drainage opening (17).

18 Claims, 4 Drawing Sheets

(58) Field of Classification Search
CPC ...... A61M 25/0111; A61M 2025/0046; A61M 25/0009; A61M 25/0015
See application file for complete search history.

(56) References Cited

U.S. PATENT DOCUMENTS

| | | | | |
|---|---|---|---|---|
| 5,180,364 A * | 1/1993 | Ginsburg | ........... | A61M 25/0075 604/510 |
| 5,312,357 A * | 5/1994 | Buijs | ................. | A61M 25/0102 604/164.01 |
| 5,334,154 A * | 8/1994 | Samson | ............ | A61M 25/0023 604/102.03 |
| 5,662,619 A * | 9/1997 | Zarate | ................. | A61M 1/3661 604/246 |
| 5,976,114 A * | 11/1999 | Jonkman | ............. | A61M 25/001 604/272 |
| 6,063,063 A * | 5/2000 | Harboe | ................. | A61M 25/00 604/93.01 |
| 8,137,337 B2 | 3/2012 | Hakky et al. | | |
| 8,317,775 B2 | 11/2012 | House | | |
| 8,888,747 B2 | 11/2014 | House | | |
| 11,701,489 B2 | 7/2023 | Hannon et al. | | |
| 2003/0060807 A1 | 3/2003 | Tanghoj et al. | | |
| 2006/0142702 A1 * | 6/2006 | Sievers | ............... | A61M 1/3659 604/264 |
| 2006/0253063 A1 * | 11/2006 | Schweikert | ....... | A61M 25/0068 604/6.16 |
| 2009/0054825 A1 * | 2/2009 | Melsheimer | ........ | A61M 25/007 604/6.16 |
| 2010/0280498 A1 * | 11/2010 | Olsen | ................ | A61M 25/0015 83/16 |
| 2011/0130745 A1 * | 6/2011 | Shevgoor | .......... | A61M 25/0009 604/523 |
| 2013/0085438 A1 * | 4/2013 | MacMeans | ......... | A61M 25/007 604/523 |
| 2013/0144223 A1 * | 6/2013 | Hewitt | ............. | A61M 25/0075 604/246 |
| 2013/0211385 A1 * | 8/2013 | Lazarus | .................. | A61M 1/87 604/540 |
| 2014/0012209 A1 * | 1/2014 | Sansoucy | .......... | A61M 25/0075 604/247 |
| 2014/0207045 A1 * | 7/2014 | Anand | ............. | A61M 25/0127 604/9 |
| 2015/0018597 A1 * | 1/2015 | Fierens | ............... | A61M 1/3621 604/523 |
| 2017/0000978 A1 * | 1/2017 | Murray | ............... | A61M 25/002 |
| 2018/0071486 A1 * | 3/2018 | O'Flynn | ........... | A61M 25/0017 |

* cited by examiner

SLEEVED HYDROPHILIC MEDICAL PRODUCTS

The present application is the U.S. National Stage of PCT Application No. PCT/US2020/048234, filed Aug. 27, 2020, which claims priority to and the benefit of U.S. Provisional Patent Application No. 62/892,301, filed Aug. 27, 2019, and U.S. Provisional Patent Application No. 62/912,229, filed Oct. 8, 2019, all of which are hereby incorporated herein by reference.

DESCRIPTION

Technical Field

The present disclosure generally relates to hydrophilic medical device products. More particularly, the present disclosure generally relates to hydrophilic urinary catheter.

Background

Several different devices in different industries are required to be hydrated prior to use and/or stored in a hydrated condition. In many instances, such devices are stored or packaged in a hydration medium, such as a liquid hydration medium. Liquid hydration mediums may be, but are not limited to, water or aqueous solutions.

One type of device wherein it may be advantageous to package the device in a hydrated stated and/or in a hydration medium is a medical device that is made from a hydrophilic material, such as a hydrophilically coated urinary catheter. In several applications, a coating of hydrophilic material is applied to the surface of a device to provide a lubricious surface. When the hydrophilic material is wetted or hydrated with a hydration medium, the hydrophilic material becomes extremely lubricous. The hydration medium may be, for example, liquid or vapor water or an aqueous solution. In the field of insertable medical devices, the lubriciousness of the hydrophilic coating can ease introduction of the device into the body and aids in reducing pain and discomfort associated with such introduction.

In devices that are required to be stored in and/or hydrated with a hydration medium, the product may include a device that is packaged in an assembly with the hydration medium, such that the device is in contact with the hydration medium. One challenge of such products is how to reduce unintentional spillage once the package is opened.

Therefore, there remains a need for package products that contain hydration mediums and hydration mediums for use in such products and methods.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter assembly, wherein the catheter assembly comprises a catheter tube having a proximal end portion and a distal end portion. The side walls of the catheter tube define a lumen. A sleeve surrounds the catheter tube and defines a cavity containing the catheter tube. Additionally, a drainage opening is located in the distal end portion of the catheter tube and goes through the side wall of the tube. The distal end portion drainage opening is in communication with the cavity of the sleeve and the lumen of the catheter tube. Also, a deflection member is associated with the distal end portion drainage opening.

In another aspect, a catheter assembly, wherein the catheter assembly comprises a catheter tube having a proximal end portion and a distal end portion. The side walls of the catheter tube define a lumen. A sleeve surrounds the catheter tube and defines a cavity containing the catheter tube. Additionally, a hydration liquid is located in the cavity of the sleeve. A drainage opening is located in the distal end portion of the catheter tube and goes through the side wall of the tube. The distal end portion drainage opening is in communication with the cavity of the sleeve and the lumen of the catheter tube. Also, a deflection member is associated with the distal end portion drainage opening, wherein the deflection member comprises a brim.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to hydrophilic medical products that have a package containing a hydrophilic medical device and a hydration medium that hydrates the hydrophilic material of the medical device. The hydrophilic materials may be materials that become lubricious when hydrated, activated or wetted with a hydration medium. The lubricious hydrophilic material may include any suitable hydrophilic polymer such as, polyvinylpyrrolidone, polyethylene oxide, polyurethanes, homo- and copolymers of acrylic and methacrylic acid, polyvinyl alcohol, etc. The hydrophilic material may be a coating on the surface of the medical device. The medical devices may include shafts or tubes that may be inserted into and advanced within a lumen of a body, such as a urethra, anus, esophagus, or fallopian tube. Such medical devices include urinary catheters, fecal catheters, endovascular catheters, endoscopes, exploratory and biopsy devices, etc. While some of the embodiments set forth below may be described in the context of urinary catheters, the disclosure is not limited to such and the features disclosed herein may be applicable to any medical tubing that is inserted into a body lumen.

Figure 1:
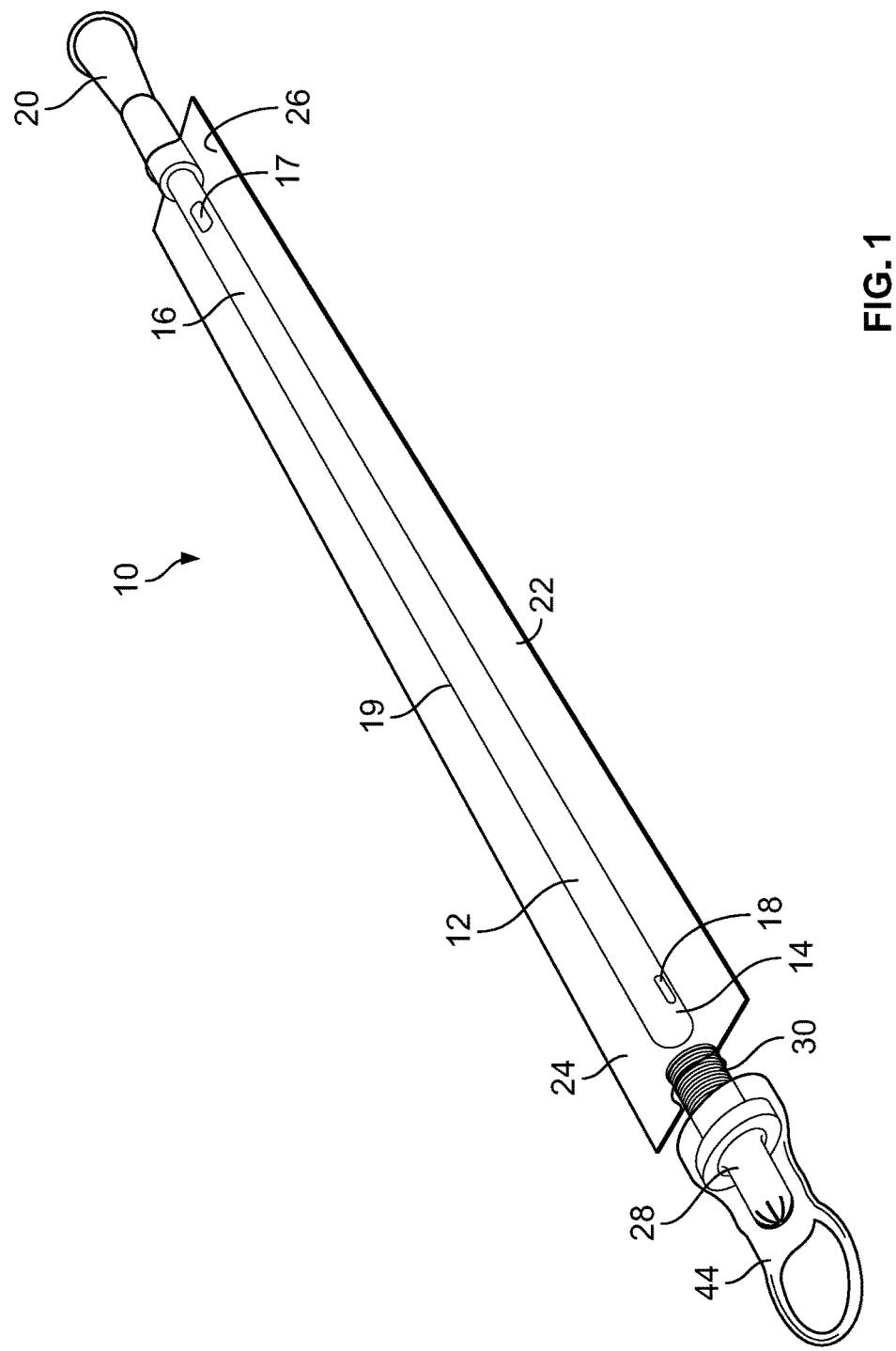
FIG. 1 is a perspective view of a catheter assembly in accordance with the present disclosure.
Figure 2:
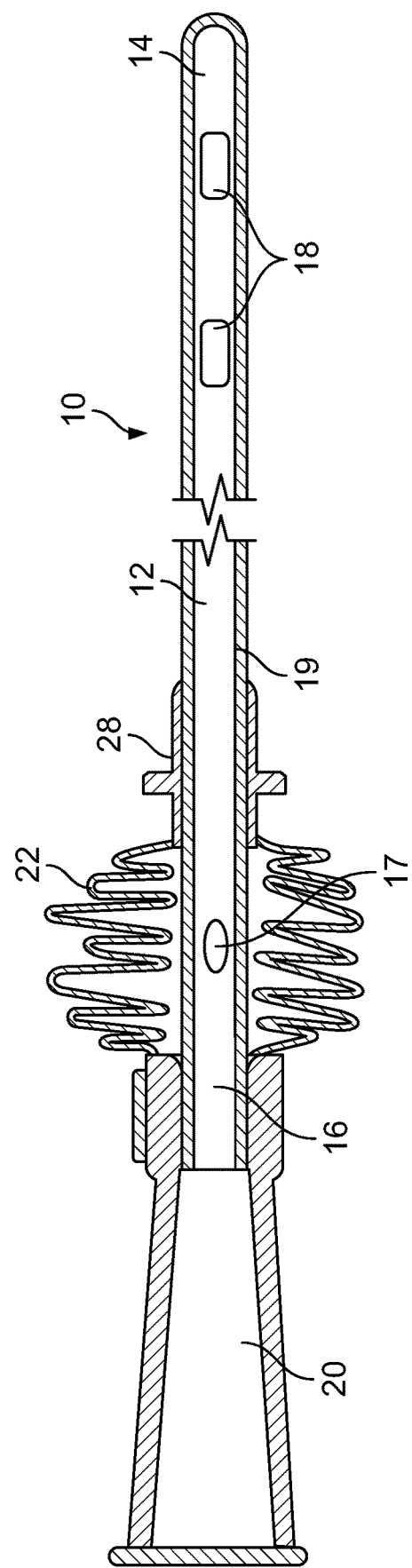
FIG. 2 is a sectional view of one embodiment of a catheter tube of the assembly in FIG. 1 in a deployed position.

Turning to FIG. 1, this figure illustrates one embodiment of a catheter assembly 10 in accordance with present disclosure, which may be part of a catheter product. The catheter assembly 10 includes an elongated catheter tube 12 with a side wall 19 defining a lumen. The catheter tube 12 also includes a proximal end portion 14 and a distal end portion 16. The proximal end portion 14 of the catheter tube 12 is suitable for insertion into a lumen or a passageway of the body, such as the urethra. The proximal end portion 14 may include proximal end portion drainage holes or eyelets 18 through the side wall 19 for draining urine from the bladder. The distal end portion 16 may include a distal end portion drainage opening 17 through the side wall 19. A drainage member 20 may be associated with the distal end portion 16 of the catheter tube 12. The catheter tube 12 includes an outer hydrophilic surface that becomes lubricious when hydrated or activated. The outer surface may be, for example, any suitable hydrophilic coating and may include any of the hydrophilic materials disclosed herein or any other suitable hydrophilic material.

The catheter assembly 10 also includes a sleeve 22, which may be a protective or barrier sleeve, that has a proximal end portion 24 and a distal end portion 26. The sleeve 22 surrounds at least a portion of the catheter tube 12 to separate and enclose the portion of the catheter tube 12 from the outside environment. In other words, the protective sleeve 22 defines an internal cavity in which the catheter tube 12 may be located. In one embodiment, the sleeve 22 extends over the length of the catheter tube 12. In addition, a hydration liquid is located in the cavity of the sleeve 22. The hydration liquid may include a liquid, such as water, along with various other components. The hydration liquid may be in a foamed or unfoamed state. Optionally, an insertion aid 28 may be located at the proximal end portion 24 of the sleeve 22. When an insertion aid 28 is present, the proximal end portion 24 of the sleeve 22 may be attached to a barrel 30 of the insertion aid 28, by for example, welding or adhesive. The distal end portion 26 of the sleeve 22 may be attached to the drainage member 20 or the catheter tube 12. An insertion aid may be used with any of the catheter assemblies disclosed herein. The introducer aid 28, optionally, may be covered by a removable protective cap 44. The removable protective cap 44 covers the introducer aid 28 and may protect the introducer aid 28 from contacting surfaces and objects prior to use.

In one embodiment, to use the catheter assembly 10, the user grasps the catheter tube 12 through the protective sleeve 22 to handle and manipulate the catheter assembly 10. The user removes protective cap 44, if one is present. If the catheter assembly 10 includes the optional insertion aid 28 shown in FIG. 1, then the user inserts the introducer aid 28 into the urethra. The user then grasps the catheter tube 12 through the sleeve 22 and advances the catheter tube 12 through the introducer aid 28, if present, and into and through the urethra until the eyelets enter the bladder. During insertion, the sleeve 22 is pushed towards the distal end portion of the sleeve 26. The hydration liquid located in the cavity of sleeve 22 drains from the cavity of the sleeve through the distal end portion drainage opening 17 and is discharged through the drainage member 20.

In an alternative embodiment, the catheter assembly 10 does not include an introducer aid 28 and the sleeve 22 has an open or closed end. When it includes an opened end, then the user grasps the catheter tube 12 through the sleeve 22 and advances the tip of the catheter tube 12 out of the open end of the sleeve 22 and into the urethra. When it includes a closed end, the user grasps the catheter tube 12 through the sleeve 22 and advances the tip of the catheter tube 12 to pierce through the closed end during deployment.

Figure 3A:
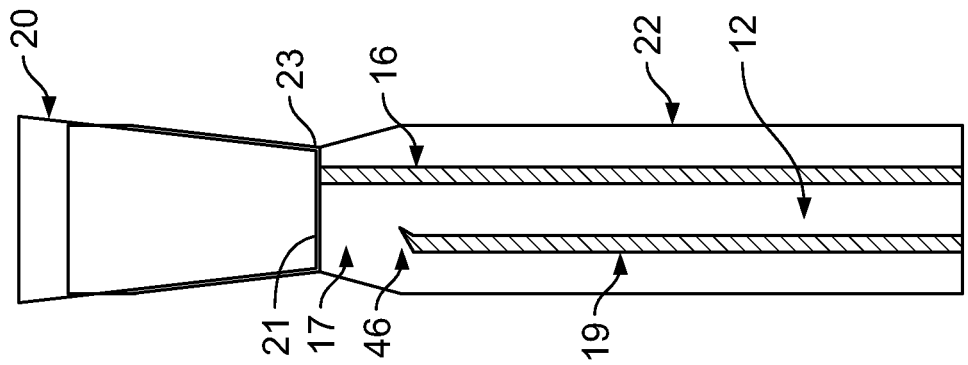
FIG. 3A is a section view of the distal end portion of an alternative embodiment of the catheter assembly of the present disclosure.
Figure 3:
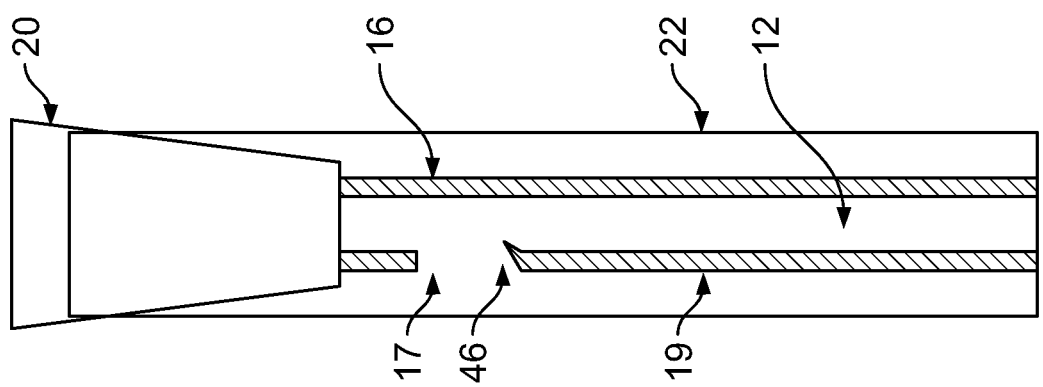
FIG. 3 is a sectional view of the distal end portion of an embodiment of the catheter assembly of the present disclosure.
Figure 4:
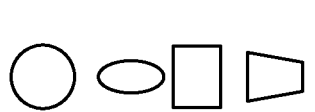
FIG. 4 is a schematic illustration showing various possible shapes of the drainage opening of the present disclosure.

Turning now to FIG. 3, this figure provides a sectional view of the distal end portion 16 of the catheter tube 12. A distal end portion drainage hole 17 through the side wall 19 is used to drain the hydration liquid located in the cavity of the sleeve 22. FIG. 4 depicts different shapes of the distal end portion drainage opening 17. The shape of the distal end portion drainage opening 17 may vary without departing from the scope of the present disclosure. In one embodiment, the distal end portion drainage opening 17 may be circular. Alternatively, the distal end portion drainage opening 17 may be any suitable shape, including but not limited to oval, rectangular, trapezoidal, etc.

The drainage opening 17 may be located at any location along the catheter tube 12 that is suitable to allow drainage of hydration medium from the cavity of the sleeve 22. For example, referring to the alternative embodiment illustrated in FIG. 3A, this embodiment of the catheter assembly is similar to the one shown in FIG. 3. However, in this embodiment, the drainage opening 17 is closely adjacent to, next to and/or abuts the drainage member 20. For example, the drainage opening 17 may abut the proximal end 21 of the drainage member 20. In addition or alternative to being closely adjacent to the proximal end 21 of the drainage member 20, the drainage opening 17 may be closely adjacent to, next to and/or abut the location of where the distal end 23 of sleeve 22 is attached to the drainage member 20. In embodiments wherein the distal end 23 of the sleeve 22 is attached directly to the catheter tube 12, the drainage opening 17 may be closely adjacent, next to or abut the location of where the distal end 23 of the sleeve 22 is attached to the catheter tube 12. The above described location of the drainage opening 17 may assist in draining the hydration medium from the cavity of the sleeve 22. That is, the location of the drainage opening 17, as described above, may eliminate or reduce the size of potential pooling spots/locations within the cavity of the sleeve 22. Such pooling spots can have the tendency to trap hydration medium and prevent it from draining from drainage opening 17. Thus, if pooling spots are eliminated or reduced in size, it is more likely for the hydration medium to drain from the drainage opening 17.

Figure 6:
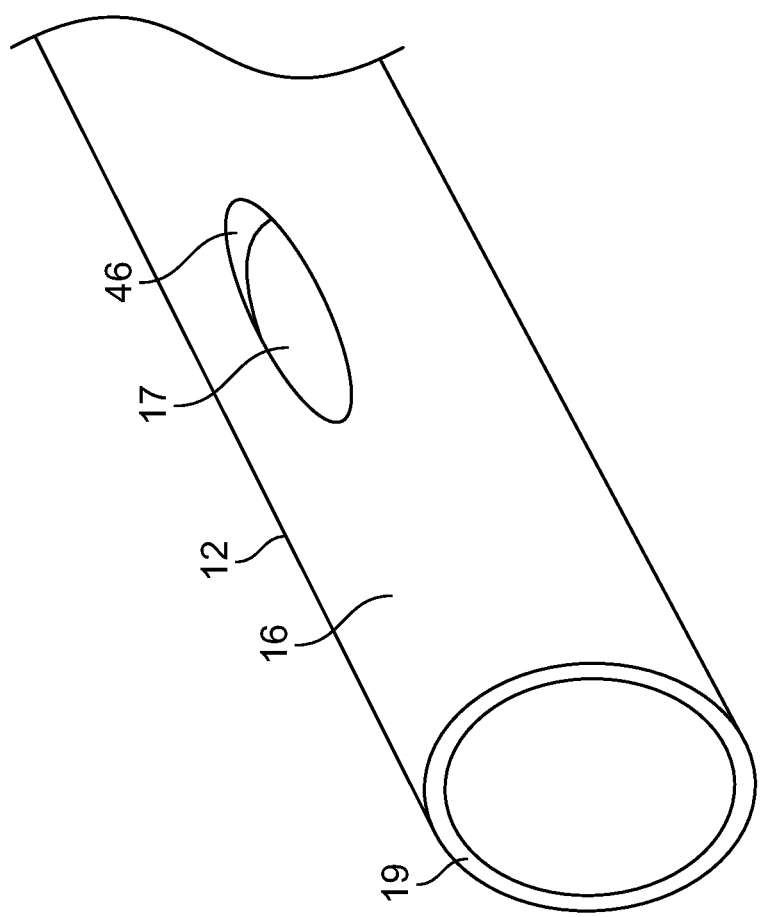
FIG. 6 is a perspective view of the distal end portion of the catheter tube of an embodiment of the catheter assembly of the present disclosure.
Figure 5:
FIG. 5 is an enlarged sectional view of embodiments of the shape of a deflection member in association with the distal end drainage opening in accordance with the present disclosure.

Referring to FIGS. 4, 5 and 6, a deflection member 46 is associated with the distal end portion drainage opening 17. The deflection member 46 may comprise a protrusion that extends into the lumen of the catheter tube 12. The deflection member may be a brim. The shape of the deflection member may vary without departing from the scope of the present disclosure. FIG. 5 depicts various shapes of the deflection member 46. In one embodiment, the deflection member 46 may be a sharp protrusion. In another embodiment, the deflection member 46 may be a rounded protrusion. As the user inserts catheter tube 12 into a urethra, the hydration liquid will be drained through the distal end portion drainage opening 17. The deflection member may guide the hydration liquid towards the drainage member 20. In addition, when urine approaches the distal end portion 16 of the catheter tube 12, the urine may be deflected by the deflection member 46 to guide the urine away from the drainage opening 17 and towards the drainage member 20. This would keep the urine from escaping through the distal end portion drainage opening 17 and into the sleeve 22.

Turning now to FIG. 6, this figure illustrates a perspective view of the distal end portion 16 of the catheter tube 12. The deflection member 46 extends into the lumen of the catheter tube 12. In one embodiment, the deflection member 46 may extend at least partially around or along a periphery of the distal end portion drainage opening 17. In another embodiment, the deflection member 46 may extend around about 50% of the periphery of the distal end portion drainage opening 17. In yet another embodiment, the deflection member 46 may extend around less than 50% of the periphery of the distal end portion drainage opening 17. Furthermore, when the drainage opening 17 has a polygonal shape, such as a rectangle, the deflection member extending along the periphery may extend along the edges of the polygon.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A catheter assembly comprising:
   a catheter tube having a proximal end portion and a distal end portion, the catheter tube having a side wall defining a lumen;
   a sleeve surrounding the catheter tube and defining a cavity containing the catheter tube;
   a drainage opening located in the distal end portion of the catheter tube and through the side wall of the catheter tube, the drainage opening being in communication with the cavity of the sleeve and the lumen of the catheter tube; and
   a deflection member associated with only a proximal portion of the drainage opening, wherein the deflection member extends into the lumen.

2. The catheter assembly of claim 1, wherein the deflection member comprises a brim.

3. The catheter assembly of claim 1, comprising a drainage member associated to the distal end portion of the catheter tube.

4. The catheter assembly of claim 3, wherein the drainage opening abuts a proximal end portion of the drainage member.

5. The catheter assembly of claim 3, wherein a distal end of the sleeve is sealed to the drainage member.

6. The catheter assembly of claim 5 wherein the drainage opening abuts a location wherein the sleeve is sealed to the drainage member.

7. The catheter assembly of claim 1, wherein the deflection member extends at least partially along a periphery of the drainage opening.

8. The catheter assembly of claim 7, wherein the deflection member extends around about 50% of the periphery of the drainage opening.

9. The catheter assembly of claim 7, wherein the deflection member extends around less than 50% of the periphery of the drainage opening.

10. The catheter assembly of claim 1, wherein the deflection member extends as a sharp protrusion.

11. The catheter assembly of claim 1, wherein the deflection member extends as a rounded protrusion.

12. The catheter assembly of claim 1, wherein a proximal end of the sleeve is sealed to an introducer aid.

13. The catheter assembly of claim 1, wherein a hydration liquid is located in the cavity of the sleeve.

14. The catheter assembly of claim 1, wherein a shape of the drainage opening comprises a circle, oval, rectangle, or trapezoid.

15. A catheter assembly, comprising:
    a catheter tube having a proximal end portion and a distal end portion, the catheter tube having a sidewall defining a lumen;
    a sleeve surrounding the catheter tube and defining a cavity containing the catheter tube;
    a hydration liquid located in the cavity of the sleeve;
    a drainage opening located in the distal end portion of the catheter tube and through the sidewall of the catheter tube, the drainage opening being in communication with the cavity of the sleeve and the lumen of the catheter tube; and
    a deflection member associated with the drainage opening, wherein the deflection member comprises a brim located only at a proximal portion of the drainage opening and extending into the lumen.

16. The catheter assembly of claim 15, comprising a drainage member associated to the distal end portion of the catheter tube.

17. The catheter assembly of claim 15, wherein the deflection member extends at least partially along a periphery of the drainage opening.

18. The catheter assembly of claim 17, wherein the deflection member extends around about 50% of the periphery of the drainage opening.

* * * * *